US005089512A

United States Patent [19]

[11] Patent Number: 5,089,512

[45] Date of Patent: Feb. 18, 1992

Wilson et al.

[54] THIAZOLE DERIVATIVES

[75] Inventors: John R. H. Wilson, Rainham; Indu Sawhney, Mainstone, both of England

[73] Assignee: Shell Research Limited, United Kingdom

[21] Appl. No.: 513,239

[22] Filed: Apr. 23, 1990

[30] Foreign Application Priority Data

Apr. 27, 1989 [GB] United Kingdom ................ 8909735
Apr. 27, 1989 [GB] United Kingdom ................ 8909736
Apr. 27, 1989 [GB] United Kingdom ................ 8909739

[51] Int. Cl.$^5$ .................. C07D 277/30; A61K 31/415

[52] U.S. Cl. .................................. 514/365; 548/186; 548/187; 548/193; 548/194; 548/203; 548/204

[58] Field of Search ............... 548/204, 203, 193, 194, 548/186, 187; 514/365

[56] References Cited

PUBLICATIONS

Burkhouse, Synthesis 1984 (330–2).

Primary Examiner—Robert Gerstl

[57] ABSTRACT

The invention provides thiazole derivatives of the general formula I:

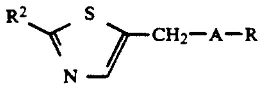

(I)

or acid-addition salts or metal salt complexes thereof, in which R represents an optionally substituted phenyl group; A represents a group $C{=}O$, $C{=}N{-}OR^1$ or

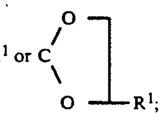

$R^1$ represents a hydrogen atom or an optionally substituted alkyl, alkenyl or aralkyl group; and $R^2$ represents a hydrogen or halogen atom or an alkyl, haloalkyl, alkoxy, haloalkoxy, alkylthio, hydroxyl, cyano, nitro, amino, alkylamino or dialkylamino group; processes for their preparation; compositions containing such compounds and their use as fungicides.

10 Claims, No Drawings

THIAZOLE DERIVATIVES

This invention relates to certain thiazole derivatives, a process for their preparation, compositions containing such compounds and their use as fungicides.

According to the present invention there is provided a compound of the general formula

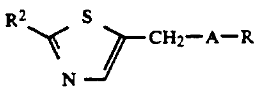

(I)

or an acid-addition salt or metal salt complex thereof, in which R represents an optionally substituted phenyl group; A represents a group C=O, C=N—OR$^1$ or 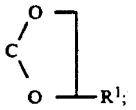;

$R^1$ represents a hydrogen atom or an optionally substituted alkyl, alkenyl or aralkyl group; and $R^2$ represents a hydrogen or halogen atom or an alkyl, haloalkyl, alkoxy, haloalkoxy, alkylthio, hydroxyl, cyano, nitro, amino, alkylamino or dialkylamino group.

When the compounds of this invention contain an alkyl or alkenyl substituent group, this may be linear or branched and may contain up to 12, preferably up to 8, carbon atoms.

When any of the foregoing substituents are designated as being optionally substituted, the substituent groups which are optionally present may be any one or more of those customarily employed in the development of pesticidal compounds, and/or the modification of such compounds to influence their structure/ activity, persistence, penetration or other property. Specific examples of such substituents include, for example, halogen atoms, nitro, cyano, hydroxyl, cycloalkyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl and alkylamido groups. When any of the foregoing substituents represents or contains an alkyl substituent group, this may be linear or branched and may contain up to 12, preferably up to 6, and especially up to 4, carbon atoms. A cycloalkyl group may contain from 3 to 8, preferably 3 to 6, carbon atoms.

It is preferred that R is a phenyl group, substituted by 1 to 3 halogen, especially fluorine or chlorine, atoms.

Preferably, $R^1$ represents a hydrogen atom, a $C_{1-12}$ alkyl, particularly a $C_{1-8}$ alkyl, group, a $C_{2-12}$ alkenyl, particularly a $C_{2-6}$ alkenyl and especially a $C_{2-4}$ alkenyl, group, or a benzyl group, each group being optionally substituted by one or more substituents selected from halogen atoms, nitro, cyano, hydroxyl, $C_{3-6}$cycloalkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, formyl, $C_{1-4}$ alkoxycarbonyl and carboxyl groups.

A particularly preferred sub-group of compounds of formula I is that in which R represents a fluorophenyl or dichlorophenyl group; $R^1$ represents a hydrogen atom or a methyl, ethyl, propyl, butyl, pentyl, hexyl, heptyl, cyclopropylmethyl, allyl, benzyl, chlorobenzyl, dichlorobenzyl or bromobenzyl group; and $R^2$ represents a hydrogen atom.

It should also be appreciated that the compounds of formula I in which A represents a group C=N-OR$^1$ are capable of existing as different geometric isomers and the compounds of formula I in which A represents a group

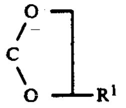

are capable of existing as different geometric and optical isomers. The invention thus includes both the individual isomers and mixtures of such isomers.

The present invention also provides a process for the preparation of a compound of formula I as defined above or an acid-addition salt or metal salt complex thereof which comprises (a) reacting a compound of the general formula

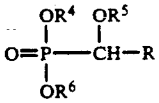

(II)

in which R is defined above and $R^4$, $R^5$ and $R^6$, which may be the same or different, represent an alkyl, cycloalkyl, phenyl or benzyl group, with a compound of the general formula

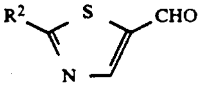

(III)

in which $R^2$ is as defined above, in the presence of a base;

(b) if desired, reacting the compound of formula I obtained in (a) with a compound of the general formula $R^1$-O-NH$_2$ (IV)

in which $R^1$ is as defined above, or with an acid-addition salt thereof;

(c) if desired, reacting the compound of formula I obtained in (a) with a compound of the general formula

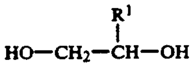

(V)

in which $R^1$ is as defined above, in the presence of a Lewis acid; and (d) if desired, reacting the compound of formula I obtained in (a), (b) or (c) with a suitable acid or metal salt to form an acid-addition salt or metal salt complex thereof.

A particularly preferred compound of formula II is that in which $R^4$ and $R^6$ both represent an ethyl group and $R^5$ represents a methyl group.

Suitable bases which may be used in step (a) of the above process include lithium diisopropylamide, potassium tert-butoxide, sodium hydride and, most preferably, butyl lithium.

Step (a) is conveniently carried out in the presence of a solvent. Suitable solvents include dimethylformamide, dimethylsulphoxide and ethers, particularly tetrahydrofuran. The reaction is suitably carried out at a temperature from −100° C. to 100° C., the preferred reaction temperature being −80° C. to 70° C.

If a compound of general formula IV is used in step (b), it is preferred that this is generated in situ. If an acid-addition salt of the compound of general formula IV is used, the process is suitably carried out in the presence of a base, such as sodium acetate.

Step (b) is conveniently carried out in the presence of a solvent. Suitable solvents include dimethylformamide, dimethylsulphoxide, ethers, such as tetrahydrofuran, aromatic compounds and alcohols, particularly methanol and ethanol. The reaction is suitably carried out at a temperature of 0° C. to 100° C., the preferred reaction temperature being 15° C. to 80° C.

In step (c), it is preferred that the Lewis acid is chlorotrimethylsilane, iodotrimethylsilane or a mixture of these two compounds or a mild protic acid such as para-toluenesulphonic acid or methanesulphonic acid.

Step (c) may be carried out in the presence of an inert solvent. Suitable solvents include aromatic compounds, such as xylene. Alternatively, an excess of the compound of formula V may serve as solvent. The reaction is suitably carried out at a temperature from 0° C. to 170° C., the preferred reaction temperature being from 15° C. to 150° C.

Compounds of formula II may be prepared according to the method described by D. Burkhouse and H. Zimmer in Synthesis, 1984, 330. Compounds of formula III in which $R^2$ is other than alkyl may be prepared by reacting thiourea with 2-bromo-1,3-propanedial and then reacting the 2-aminothiazole carboxaldehyde hydrobromide thus obtained with amyl nitrite. Compounds of formula III in which $R^2$ is alkyl may be prepared by reacting an appropriate alkyl thioamide with 2-bromo-1,3-propanedial in an analogous way. 2-bromo-1,3-propanedial may be prepared according to the method described by S. Trofimenko in J. Org. Chem., 1963, 28, 3243.

Compounds of formula IV and V are known compounds or can be prepared by processes analogous to known processes.

The compounds of general formula I have been found to have fungicidal activity. Also, certain compounds of formula I have been found to exhibit vapour activity. Accordingly, the invention further provides a fungicidal composition which comprises a carrier and, as active ingredient, a compound of formula I or an acid-addition salt or metal salt complex thereof as defined above. A method of making such a composition is also provided which comprises bringing a compound of formula I as defined above, or an acid-addition salt or metal salt complex thereof, into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminum silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example, kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least lo carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½–10% w of active ingredient. Granules are usually prepared to have a size between 10 and 100 BS mesh (1.676 - 0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1-50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The invention still further provides the use as a fungicide of a compound of the general formula I as defined above or an acid-addition salt or metal salt complex thereof or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop plants against fungal attack. Typical crops which may be protected include vines, grain crops such as wheat and barley, rice and tomatoes. The duration of protection is normally dependent on the individual compound selected, and also a variety of external factors, such as climate, whose impact is normally mitigated by the use of a suitable formulation.

The invention is further illustrated by the following examples.

EXAMPLE 1

Preparation of 1-(2,4-dichlorophenyl)-2-(5-thiazolyl)ethanone ($R$=2,4-dichlorophenyl; $A=C=0$; $R^2$=hydrogen)

(i) Preparation of 5-thiazolecarboxaldehyde

Thiourea (33 g, 0.44 mol) was added to a solution of 2-bromo-1,3-propanedial (66 g, 0.44 mol) in acetone (1 liter) and the resulting mixture was stirred vigorously under reflux for 1 hour. After cooling to room temperature, the solid product was filtered off and dried to give 2-aminothiazolecarboxaldehyde hydrobromide (85 g) as a yellow solid, m.pt. 126° C.

A solution of 2-aminothiazolecarboxaldehyde hydrobromide (35 g, 0.168 mol) in methanol was neutralised with sodium methoxide (9 g, 0.168 mol). The methanol was then evaporated off under reduced pressure to leave a solid which was suspended in tetrahydrofuran (200 ml) and added slowly to a refluxing solution of amyl nitrite (31 g) in tetrahydrofuran (300 ml). The resultant mixture was refluxed for one hour, cooled, filtered and then concentrated under reduced pressure. Diethyl ether (400 ml) was added to the residue and the mixture was then stirred for one hour, filtered and concentrated. The residue was then chromatographed on silica gel using 2:1 petroleum ether:diethyl ether as eluant to give 5-thiazolecarboxaldehyde (4.4 g) as a yellow solid, m.pt. 15° C.

(ii) Preparation of 1-(2,4-dichlorophenyl)-2-(5-thiazolyl)ethanone

Butyl lithium (2.5M, 14 ml) in hexane wa added dropwise to a solution of diethyl (2,4-dichlorophenyl)methoxymethyl phosphonate (12.8 g, 39 mmol) in tetrahydrofuran (150 ml) at −78° C. under an atmosphere of nitrogen. The resulting deep red solution was stirred for 10 minutes and then treated with 3.7 g (32 mmol) of the 5-thiazolecarboxaldehyde obtained in (i) dissolved in tetrahydrofuran (50 ml). After a further hour at −78° C., the reaction mixture was allowed to warm to room temperature whereupon it was treated with water and then acidified with concentrated sulphuric acid (35 ml) and refluxed for 20 hours. After cooling, the tetrahydrofuran was evaporated and the aqueous residue neutralised with sodium carbonate and then extracted with ethyl acetate (2×200 ml). The combined organic extract was washed with saturated sodium chloride solution, dried and concentrated. The residue was then chromatographed on silica using 7:3 petroleum ether:ethyl acetate as eluant to give 1-(2,4-dichlorophenyl)-2-(5-thiazolyl)ethanone (5.75 g) as a pale yellow solid, m.pt. 75°-77° C.

Analysis

Calc: C:48.5; H:2.6; N:5.1%

Found: C:47.9; H:2.6; N:5.0%

EXAMPLE 2

Preparation of 1-(2,4-dichlorophenyl)-2-(5-thiazolyl)ethanone O-ethyloxime R=2,4-dichlorophenyl; A=C=N-OR$^1$; R$^1$=ethyl; R$^2$=hydrogen)

A mixture of the 1-(2,4-dichlorophenyl)-2-(5-thiazolyl)ethanone (1.1 g, 4 mmol) obtained in Example 1, sodium acetate (1.64 g, 20 mmol) and O-ethylhydroxylamine hydrochloride (1.95 g, 20 mmol) was refluxed in methanol (80 ml) for 20 hours under an atmosphere of nitrogen. After cooling to room temperature, water (50 ml) was added and the reaction mixture was then concentrated under reduced pressure. The aqueous residue was made basic with sodium carbonate and then extracted with ethyl acetate (2×200 ml). The combined organic extract was then washed with saturated sodium chloride solution, dried and concentrated. Chromatography of the residue on silica using 4:1 petroleum ether (40–60):ethyl acetate as eluant gave, as compound A, the E-isomer (0.88 g) and, as compound B, the Z-isomer (0.20 g) of 1-(2,4-dichlorophenyl)-2-(5-thiazolyl)ethanone as oils.

Analysis

E/Z mixture

Calc: C:49.5; H:3.8; N:8.8%

Found: C:51.0; H:4.3; N:8.4%

EXAMPLE 3

Preparation of 2-(2,4-dichlorophenyl)-2-(thiazol-5-ylmethyl)-1,3-dioxolane (R=2,4-dichlorophenyl; R$^1$=hydrogen; R$^2$=hydrogen;

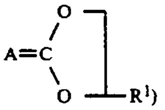

A mixture of the 1-(2,4-dichlorophenyl)-2-(5-thiazolyl)ethanone (1.49 g, 5.4 mmol) obtained in Example 1 and chlorotrimethylsilane (2.8 ml) in ethane-1,2-diol (25 ml) was stirred at 90° C. for 4 hours and then cooled to room temperature. The reaction mixture was then poured into sodium bicarbonate solution, extracted with ethyl acetate, washed with water and dried over magnesium sulphate. Evaporation of the solvent under reduced pressure afforded a dark brown oil and flash chromatography of this oil on a silica gel column using 1:9 (v/v) ethyl acetate: petroleum 60–80 yielded 2-(2,4-dichlorophenyl)-2-(thiazol-5-ylmethyl)-1,3-dioxolane (0.64 g) as a yellow oil.

Analysis

Calc: C: 49.5; H: 3.8; N: 4.4%

Found: C: 51.2; H: 4.3; N: 4.3%

EXAMPLE 4

Preparation of 2-(2,4-dichlorophenyl)-2-(thiazol-5-ylmethyl)-4-methyl-1,3-dioxolane. (R=2,4-dichlorophenyl; R$^1$=methyl; R$^2$=hydrogen;

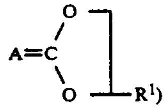

A mixture of the 1-(2,4-dichlorophenyl)-2-(5-thiazolyl)ethanone (1.3 g, 11 mmol) obtained in Example 1, chlorotrimethylsilane (6 ml) and iodotrimethylsilane (2 ml) in propane-1,2-diol was stirred at 110° C. for 4 hours and then cooled to room temperature. The reaction mixture was then poured into sodium bicarbonate solution, extracted with ethyl acetate, washed with water and dried over magnesium sulphate. Evaporation of the solvent under reduced pressure afforded a dark brown oil and flash chromatography of this oil on a silica gel column using 5:95 (v/v) diethyl ether: dichloromethane as eluant yielded 2-(2,4-dichlorophenyl)-2-(thiazol-5'-ylmethyl)-4-methyl-1,3-dioxolane (1.89 g) as a mixture of isomèrs. Further flash chromatography of the product on a silica gel column using 1:9 (v/v) ethyl acetate: petroleum 60–80 as eluant afforded two enantiomeric pairs of the desired product as sample A (2R,4R)(2S,4S) 0.49 g and sample B (2R,4S)(2S,4R), 0.45 g.

M+

Calc: 330.012

Found:

Sample A: 330.014

Sample B: 330.013

EXAMPLE 5

Preparation of 2-(4-fluorophenyl)-2-(thiazol-5-ylmethyl)-4-methyl-1,3-dioxolane R=4-fluorophenyl; R$^1$=methyl; R$^2$=hydrogen;

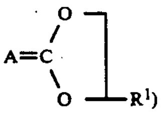

A mixture of 1-(4-fluorophenyl)-2-(5-thiazolyl)ethanone (0.75 g, 3.3 mmol) obtained by a process analogous to that described in Example 1, propane-1,2-diol (2 ml) and methanesulphonic acid (0.5 ml) in xylene (30 ml) was stirred at reflux under an atmosphere of nitrogen for 2 hours using a Dean and Stark apparatus and then cooled to room temperature. The reaction mixture was then poured into water, extracted with ethyl acetate and dried over magnesium sulphate. Evaporation of the solvent under reduced pressure afforded a dark brown oil and flash chromatography of this oil on a silica gel column using 2:8 (v/v) ethyl acetate: petroleum 60–80 yielded two enantiomeric pairs of 2-(4-fluorophenyl)-2-(thiazol-5-ylmethyl)-4-methyl-1,3-dioxolane as Sample A (2R,4R)(2S,4S) 0.17 g and Sample B (2R,4S)(2S,4R), 0.11 g, as oils.

Analysis (Mixture of A and B)

Calc: C: 60.2; H: 5.0; N: 5.0%

Found C: 6? .5; H: 5.9; N: 4.6%

EXAMPLE 6 to 35

By processes similar to those described in Examples 1 to 5 above, further compounds according to the invention were prepared as detailed in Table I below. In this table, the compounds are identified by reference to formula I. High resolution mass spectroscopy and C,H,N analysis data for the compounds of Examples 6 to 35 are given in Table IA below.

TABLE I

| Example No. | Isomers | R | A | $R^1$ | $R^2$ |
|---|---|---|---|---|---|
| 6 | — | 4-fluorophenyl | C=O | — | H |
| 7 | — | 4-chlorophenyl | C=O | — | H |
| 8A | E | 2,4-dichlorophenyl | $C{=}N{-}OR^1$ | $-CH_3$ | H |
| 8B | Z | 2,4-dichlorophenyl | $C{=}N{-}OR^1$ | $-CH_3$ | H |
| 9A | E | 2,4-dichlorophenyl | $C{=}N{-}OR^1$ | $-CH_2CH_2CH_3$ | H |
| 9B | Z | 2,4-dichlorophenyl | $C{=}N{-}OR^1$ | $-CH_2CH_2CH_3$ | H |
| 10A | E | 2,4-dichlorophenyl | $C{=}N{-}OR^1$ | $-CH(CH_3)_2$ | H |
| 10B | Z | 2,4-dichlorophenyl | $C{=}N{-}OR^1$ | $-CH(CH_3)_2$ | H |
| 11A | E | 2,4-dichlorophenyl | $C{=}N{-}OR^1$ | $-(CH_2)_3CH_3$ | H |
| 11B | Z | 2,4-dichlorophenyl | $C{=}N{-}OR^1$ | $-(CH_2)_3CH_3$ | H |
| 12A | E | 2,4-dichlorophenyl | $C{=}N{-}OR^1$ | $-CH_2CH(CH_3)_2$ | H |
| 12B | Z | 2,4-dichlorophenyl | $C{=}N{-}OR^1$ | $-CH_2CH(CH_3)_2$ | H |
| 13A | E | 2,4-dichlorophenyl | $C{=}N{-}OR^1$ | $-CH(CH_3)(C_2H_5)$ | H |
| 13B | Z | 2,4-dichlorophenyl | $C{=}N{-}OR^1$ | $-CH(CH_3)(C_2H_5)$ | H |
| 14A | E | 2,4-dichlorophenyl | $C{=}N{-}OR^1$ | $-(CH_2)_4CH_3$ | H |
| 14B | Z | 2,4-dichlorophenyl | $C{=}N{-}OR^1$ | $-(CH_2)_4CH_3$ | H |
| 15 | E | 2,4-dichlorophenyl | $C{=}N{-}OR^1$ | $-(CH_2)_5CH_3$ | H |
| 16A | E | 2,4-dichlorophenyl | $C{=}N{-}OR^1$ | $-(CH_2)_6CH_3$ | H |
| 16B | Z | 2,4-dichlorophenyl | $C{=}N{-}OR^1$ | $-(CH_2)_6CH_3$ | H |
| 17A | E | 2,4-dichlorophenyl | $C{=}N{-}OR^1$ | cyclopropylmethyl | H |
| 17B | Z | 2,4-dichlorophenyl | $C{=}N{-}OR^1$ | cyclopropylmethyl | H |
| 18A | E | 2,4-dichlorophenyl | $C{=}N{-}OR^1$ | $-CH_2CH{=}CH_2$ | H |
| 18B | Z | 2,4-dichlorophenyl | $C{=}N{-}OR^1$ | $-CH_2CH{=}CH_2$ | H |
| 19A | E | 2,4-dichlorophenyl | $C{=}N{-}OR^1$ | benzyl | H |
| 19B | Z | 2,4-dichlorophenyl | $C{=}N{-}OR^1$ | benzyl | H |
| 20A | E | 2,4-dichlorophenyl | $C{=}N{-}OR^1$ | 4-chlorobenzyl | H |
| 20B | Z | 2,4-dichlorophenyl | $C{=}N{-}OR^1$ | 4-chlorobenzyl | H |
| 21A | E | 2,4-dichlorophenyl | $C{=}N{-}OR^1$ | 2,4-dichlorobenzyl | H |
| 21B | Z | 2,4-dichlorophenyl | $C{=}N{-}OR^1$ | 2,4-dichlorobenzyl | H |
| 22 | E | 2,4-dichlorophenyl | $C{=}N{-}OR^1$ | 4-bromobenzyl | H |
| 23 | E | 2,4-dichlorophenyl | $C{=}N{-}OR^1$ | $-CH_2-C{\equiv}CH$ | H |
| 24A | E | 4-fluorophenyl | $C{=}N{-}OR^1$ | $-CH_3$ | H |
| 24B | Z | 4-fluorophenyl | $C{=}N{-}OR^1$ | $-CH_3$ | H |
| 25 | E | 4-fluorophenyl | $C{=}N{-}OR^1$ | $-CH_2CH_3$ | H |
| 26A | E | 4-fluorophenyl | $C{=}N{-}OR^1$ | benzyl | H |
| 26B | Z | 4-fluorophenyl | $C{=}N{-}OR^1$ | benzyl | H |
| 27 | E | 4-chlorophenyl | $C{=}N{-}OR^1$ | $-CH_3$ | H |
| 28A | E | 4-chlorophenyl | $C{=}N{-}OR^1$ | $-CH_2CH_3$ | H |
| 28B | Z | 4-chlorophenyl | $C{=}N{-}OR^1$ | $-CH_2CH_3$ | H |
| 29 | E | 4-chlorophenyl | $C{=}N{-}OR^1$ | $-(CH_2)_4CH_3$ | H |
| 30A | E | 4-chlorophenyl | $C{=}N{-}OR^1$ | $-CH_2-CH{=}CH_2$ | H |
| 30B | Z | 4-chlorophenyl | $C{=}N{-}OR^1$ | $-CH_2-CH{=}CH_2$ | H |
| 31 | E | 4-chlorophenyl | $C{=}N{-}OR^1$ | benzyl | H |
| 32A | (2S,4S) | 2,4-dichlorophenyl | 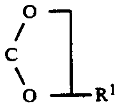 | $-CH_3$ | —H |
| 32B | (2R,4S) | 2,4-dichlorophenyl | 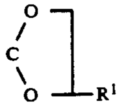 | $-CH_3$ | —H |
| 33 | (2R,4R) (2S,4S) (2R,4S) & (2S,4R) | 2,4-dichlorophenyl | 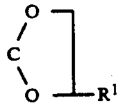 | $-C_2H_5$ | —H |
| 33A | (2R,4R) (2S,4S) | 2,4-dichlorophenyl | 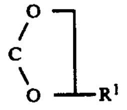 | $-C_2H_5$ | —H |
| 34 | (2R,4R) (2S,4S) (2R,4S) & (2S,4R) | 2,4-dichlorophenyl | 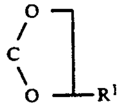 | $-CH_2CH_2CH_3$ | —H |

TABLE I-continued
| Example No. | Isomers | R | A | $R^1$ | $R^2$ |
|---|---|---|---|---|---|
| 35 | | 4-fluorophenyl | 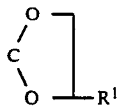 | —H | —H |
TABLE IA
| Example No. | M.pt (°C.) | Analysis % M+ Calc. | M+ Found | C Calc. | C Found | H Calc. | H Found | N Calc. | N Found |
|---|---|---|---|---|---|---|---|---|---|
| 6 | 49-50 | | | | | | | | |
| 7 | 60-62 | | | 55.7 | 55.6 | 3.4 | 3.6 | 5.9 | 5.9 |
| 8A<br>8B | | 299.98907 | 299.9884 | | | | | | |
| 9A<br>9B | | | | 51.1 | 51.0 | 4.3 | 4.4 | 8.5 | 8.6 |
| 10A<br>10B | | | | 51.1 | 51.3 | 4.2 | 4.4 | 8.5 | 7.4 |
| 11A<br>11B | | | | 52.5 | 52.9 | 4.7 | 4.6 | 8.2 | 8.3 |
| 12A<br>12B | | | | 52.5 | 52.5 | 4.7 | 4.8 | 8.2 | 8.3 |
| 13A<br>13B | | | | 52.5 | 52.7 | 4.7 | 4.8 | 8.2 | 8.4 |
| 14A<br>14B | | | | 53.8 | 53.2 | 5.1 | 4.7 | 7.8 | 7.9 |
| 15 | | | | 54.9 | 56.6 | 5.3 | 5.4 | 7.5 | 7.3 |
| 16A<br>16B | | | | 56.1 | 56.3 | 5.7 | 6.2 | 7.3 | 7.2 |
| 17A<br>17B | | 340.02037 | 340.02028 | | | | | | |
| 18A<br>18B | | 326.0047 | 326.0036 | | | | | | |
| 19A<br>19B | | 376.0203 | 376.0196 | 57.3 | 59.0 | 3.7 | 4.2 | 7.4 | 7.4 |
| 20A<br>20B | | | | 52.5 | 52.5 | 3.2 | 3.2 | 6.8 | 6.9 |
| 21A<br>21B | | | | 48.4 | 48.6 | 2.7 | 2.7 | 6.3 | 6.7 |
| 22 | | | | 47.4 | 47.4 | 2.9 | 3.1 | 6.1 | 6.4 |
| 23 | | 324.9970 | 324.9990 | | | | | | |
| 24A<br>24B | | | | 57.6 | 58.0 | 4.4 | 4.5 | 11.2 | 11.1 |
| 25 | | | | 59.1 | 59.7 | 4.9 | 5.1 | 10.6 | 10.0 |
| 26A<br>26B | | | | 66.3 | 66.9 | 4.6 | 5.1 | 8.5 | 8.8 |
| 27 | | | | 54.1 | 54.1 | 4.1 | 4.5 | 10.5 | 10.5 |
| 28A<br>28B | | | | 55.7 | 55.1 | 4.6 | 4.9 | 10.0 | 9.8 |
| 29 | | | | 59.6 | 59.4 | 5.9 | 6.4 | 8.7 | 7.9 |
| 30A<br>30B | | 57.5 | 57.5 | 4.5 | 4.6 | 9.6 | 9.3 | | |
| 31 | | | 63.5 | 63.5 | 3.8 | 4.1 | 8.2 | 7.9 | |
| 32A | | 330.013 | | | | | | | |
| 32B | | 330.012 | | | | | | | |
| 33 | | 344.0279 | | | | | | | |
| 33A | | 344.027 | | | | | | | |
| 34 | | 358.0441 | | | | | | | |
| 35 | | | 58.8 | 60.2 | 4.6 | 4.8 | 5.3 | 5.5 | |

EXAMPLE 36

The fungicidal activity of compounds of the invention was investigated by means of the following tests.

(a) Antisporulant activity against vine downy mildew (Plasmopara viticola; Pva)

The test is a direct antisporulant one using a foliar spray. The lower surfaces of leaves of whole vine plants (cv Cabernet Sauvignon) are inoculated by spraying with an aqueous suspension containing $10^4$ zoosporangia/ml 2 days prior to treatment with the test compound. The inoculated plants are kept for 24 hours in a high humidity compartment, then 24 hours at glasshouse ambient temperature and humidity. Infected leaves are sprayed on their lower surfaces with a solution of active material in 1:1 water/acetone containing 0.04% "TWEEN 20" (Trade Mark; a polyoxyethylene sorbitan ester surfactant). The spraying is carried out with a moving track sprayer giving an application rate of lkg/ha. After spraying, the plants are returned to normal glasshouse conditions for 96 hours and are then transferred to the high humidity compartment for 24 hours to induce sporulation, prior to assessment. Assessment is based on the percentage of the leaf area covered by sporulation compared with that on control leaves.

(b) Direct protectant activity against vine downy mildew (Plasmopara viticola; Pvp)

The test is a direct protectant one using a foliar spray. The lower surfaces of leaves of whole vine plants (cv Cabernet Sauvignon) are sprayed with the test compound at a dosage of 1 kilogram of active material per hectare using a track sprayer as described under (a), and after a subsequent 24 hours under normal glasshouse conditions the lower surfaces of the leaves are inoculated by spraying with an aqueous solution containing $10^4$ zoosporangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(c) Direct protectant activity against vine grey mould (Botrytis cinerea; Bcp)

The test is a direct protectant one using a foliar spray. The lower surfaces of detached vine leaves (cv Cabernet Sauvignon) are sprayed with the test compound at a dosage of lkg/ha using a track sprayer as in (a). 24 hours after spraying the leaves are inoculated with droplets of aqueous suspension containing $10^5$ conidia/ml. After a further 5 days in high humidity the percentage of leaf area covered by disease is assessed.

(d) Activity against wheat leafspot (Leptosphaeria nodorum; Ln.)

The test is a direct therapeutic one, using a foliar spray. Leaves of wheat plants (cv Mardler), at the single leaf stage, are inoculated by spraying with an aqueous suspension containing $1\times10^6$ spores/ml. The inoculated plants are kept for 24 hours in a high humidity compartment prior to treatment. The plants are sprayed with a solution of the test compound at a dosage of 1 kilogram of active material per hectare using a track sprayer as described under (a). After drying, the plants are kept for 6–8 days at 20°-25° C. and moderate humidity, followed by assessment. Assessment is based on the density of lesions per leaf compared with that on leaves of control plants.

(e) Activity against barley powdery mildew (Erysiphe graminis f.sp. hordei; Eg)

The test is a direct therapeutic one, using a foliar spray. Leaves of barley seedlings, (cv. Golden Promise) are inoculated by dusting with mildew conidia one day prior to treatment with the test compound. The inoculated plants are kept overnight at glasshouse ambient temperature and humidity prior to treatment. The plants are sprayed with the test compound at a dosage of 1 kilogram of active material per hectare using a track sprayer as described under (a). After drying, plants are returned to a compartment at 20°-25° C. and moderate humidity for up to 7 days, followed by assessment. Assessment is based on the percentage of leaf area covered by sporulation compared with that on leaves of control plants.

(f) Activity against wheat brown rust (Puccinia recondita; Pr)

The test is a direct protectant one using a foliar spray. Wheat seedlings (cv Brigand) are grown to the 1-1½ leaf stage. The plants are then sprayed with the test compound at a dosage of 1 kg/ha using a track sprayer as described under (a). Test compounds are applied as solutions or suspensions in a mixture of acetone and water (50:50 v/v) containing 0.04% surfactant ("TWEEN 20"—Trade Mark).

18–24 hours after treatment, the seedlings are inoculated by spraying the plants from all sides with an aqueous spore suspension containing about $10^5$ spores/ml. For 18 hours after inoculation, the plants are kept in high humidity conditions at a temperature of 20°-22° C. Thereafter, the plants are kept in ambient glasshouse conditions, that is, in moderate relative humidity and at a temperature of 20° C.

The disease is assessed 10 days after inoculation on the basis of the percentage of the plant covered by sporulating pustules compared with that on the control plants.

(g) Activity against rice leaf blast (Pyricularia oryzae Po)

The test is a direct therapeutic one using a foliar spray. The leaves of rice seedlings (about 30 seedlings per pot) are sprayed with an aqueous suspension containing $10^5$ spores/ml 20–24 hours prior to treatment with the test compound. The inoculated plants are kept overnight in high humidity and then allowed to dry before spraying with the test compound at a dosage of 1 kilogram of active material per hectare using a track sprayer as described under (a). After treatment the plants are kept in a rice compartment at 25°-30° C. and high humidity. Assessments are made 4–5 days after treatment and are based on the density of necrotic lesions per leaf when compared with control plants.

(h) Activity against tomato early blight (Alternaria solani; As)

This test measures the contact prophylactic activity of test compounds applied as a foliar spray. Tomato seedlings (cv Outdoor Girl) are grown to the stage at which the second true leaf is expanded. The plants are treated using a track sprayer as described under (a). Test compounds are applied as solutions or suspensions in a mixture of acetone and water (50:50 v/v) containing 0.04% surfactant ("TWEEN 20"—Trade Mark).

One day after treatment the seedlings are inoculated by spraying the leaf upper surfaces with a suspension of *A. solani* conidia containing $10^4$ spores/ml. For 3 days after inoculation plants are kept moist in a glasshouse compartment at or near 100% RH and 21° C. Thereafter plants are kept under humid, but not saturated, conditions. Disease is assessed 7 days after inoculation, based on the density and spread of lesions.

(i) Activity against wheat eyespot in-vitro Pseudocercosporella herpotrichoides; PhI)

This test measures the in vitro activity of compounds against the fungus causing wheat eyespot.

The test compound is dissolved or suspended in acetone and is added to molten half strength Potato Dextrose Agar to give a final concentration of 100 ppm compound and 3.5% acetone. After the agar has set, plates are inoculated with 6 mm diameter plugs of agar/mycelium taken from a 14 day old culture of *P. herpotrichoides.*

Plates are incubated at 20° C. for 12 days and radial growth from the inoculation plug is measured.

(j) Activity against Fusarium in-vitro (Fusarium species; FsI)

This test measures the in vitro activity of compounds against a species of Fusarium that causes stem and root rots.

Compound is dissolved or suspended in acetone and added to molten half strength Potato Dextrose Agar to give a final concentration of 100 ppm compound and 3.5% acetone. After the agar has set, plates are inoculated with 6 mm diameter plugs of agar and mycelium taken from a 7 day old culture of Fusarium sp..

Plates are incubated at 20° C. for 5 days and radial growth from the plug is measured.

The extent of disease control in all the above tests is expressed as a rating compared with either an untreated control or a diluent-sprayed-control, according to the criteria:

0=less than 50% disease control
1=about 50-80% disease control
2=greater than 80% disease control The results of these tests are set out in Table II below:

TABLE II

| Compound Example | Fungicidal Activity | | | | | | | | | |
|---|---|---|---|---|---|---|---|---|---|---|
| No. | Pva | Pvp | Bcp | Ln | Eg | Pr | Po | As | PhI | FsI |
| 1 | | | | | 2 | | 1 | | | 1 |
| 2A | | 1 | 1 | 2 | 2 | 2 | 1 | 2 | 2 | 1 |
| 2B | | | 1 | 1 | | 2 | 1 | | 2 | 1 |
| 3 | | 1 | | 2 | 2 | 1 | 2 | 1 | 2 | 2 |
| 4A | | | | 2 | 2 | | 2 | 2 | 2 | 2 |
| 4B | | 2 | | 2 | 2 | | 1 | 1 | 2 | 2 |
| 5A | 1 | | | 2 | 1 | | | 1 | 2 | 2 |
| 5B | | 1 | | 1 | 1 | | | | 2 | 2 |
| 7 | 1 | | | 1 | 2 | | | | | |
| 8A | | 1 | 1 | 2 | 2 | 2 | 1 | 2 | 2 | 2 |
| 8B | | 1 | | 2 | 2 | 2 | | 1 | 2 | 2 |
| 9A | | 1 | | 2 | 2 | 2 | | 2 | 2 | 2 |
| 9B | | 1 | | 2 | 2 | | | | 2 | 1 |
| 10A | | 1 | 1 | 2 | 2 | 2 | 2 | 2 | 2 | 1 |
| 10B | | 1 | | 2 | 2 | 2 | | 1 | 2 | 2 |
| 11A | 1 | 1 | | 2 | 2 | 2 | 1 | 2 | 1 | |
| 11B | | | | 1 | 2 | | 1 | | | |
| 12A | | 2 | | 1 | 2 | 2 | | 1 | 2 | |
| 12B | 1 | 1 | | | 2 | 2 | | | 1 | |
| 13A | | 1 | | 2 | 2 | 2 | | | 2 | |

TABLE II-continued

| Compound Example | Fungicidal Activity | | | | | | | | | |
|---|---|---|---|---|---|---|---|---|---|---|
| No. | Pva | Pvp | Bcp | Ln | Eg | Pr | Po | As | PhI | FsI |
| 13B | | 2 | | 1 | 2 | 2 | | | 1 | |
| 14A | | 2 | | 1 | 2 | 2 | | | 2 | |
| 14B | | 1 | | 1 | 2 | | | | | |
| 15 | | | | 1 | 2 | 2 | 1 | 1 | 1 | |
| 16A | | | | 1 | 2 | | | 1 | 1 | |
| 16B | | | | 1 | 2 | | | | | |
| 17A | | 1 | 1 | 2 | 2 | 2 | | 1 | 2 | |
| 17B | | 1 | | 2 | 2 | 2 | | 2 | 2 | 1 |
| 18A | | 2 | | 2 | 2 | 2 | 1 | 1 | 2 | 1 |
| 18B | | 1 | | 2 | 2 | 2 | 1 | 1 | 2 | 1 |
| 19A | | 1 | | 2 | 2 | 2 | | 2 | 1 | |
| 19B | | | | 2 | 2 | 2 | | | 1 | 1 |
| 20A | | 2 | | 2 | 2 | 2 | | | 1 | |
| 20B | | 2 | | 2 | 2 | 2 | | | 1 | |
| 21A | | | | 2 | 2 | 1 | | 1 | 2 | |
| 21B | 1 | | | | 2 | | | | 1 | |
| 22 | | | | 1 | 2 | 2 | | | 1 | |
| 23 | | 1 | 2 | 2 | 2 | 2 | 1 | 2 | 2 | 1 |
| 24A | | | | 1 | | | | 1 | 2 | 2 |
| 24B | 2 | | 1 | | 2 | | | | 2 | 2 |
| 25 | | | | | 1 | | | | 2 | 1 |
| 26A | 2 | | 2 | | | | | | | |
| 26B | 1 | 1 | | 1 | 2 | 2 | 2 | | 1 | |
| 27 | | | | 1 | 2 | | | 1 | 2 | 2 |
| 28A | | | | 1 | 2 | 1 | | | 2 | 1 |
| 28B | | | | 2 | 2 | | | | 2 | 1 |
| 29 | 1 | | | 1 | 2 | | | | | |
| 30A | 1 | 1 | | 2 | 2 | | | | 1 | |
| 30B | | 1 | 1 | 2 | 2 | 1 | | 1 | 2 | |
| 31 | | 1 | | 1 | 2 | 1 | | | | |
| 32A | 1 | 1 | | 2 | 2 | | 2 | 1 | 2 | 2 |
| 32B | 1 | 2 | | 2 | 2 | | 1 | 1 | 2 | 2 |
| 33 | | | | 2 | 2 | 1 | 1 | 1 | 2 | 2 |
| 33A | | | | 2 | 2 | 1 | 1 | 1 | 2 | 2 |
| 34 | | 1 | | 2 | 2 | | | 1 | 2 | 1 |
| 35 | 1 | | 1 | 2 | 1 | | | 1 | 2 | 2 |

EXAMPLE 37

Vapour activity against barley powdery mildew (Erysiphe graminis; Eg)

Barley seedlings (cv. Golden Promise) were grown to the 1+ leaf stage in 7 cm pots and inoculated with mildew conidia one day prior to treatment with the test compound. The plants were then sprayed with a solution of the test compound in 1:1 water/acetone containing 0.04% "TWEEN 20" (Trade Mark; a polyoxyethylene sorbitan ester surfactant) at an application rate of 1 kg/ha using an air brush. The sprayed plants were then added immediately to a standardised layout of unsprayed inoculated plants within a 60 cm square perspex wall. After approximately 7 days, the percent cover by disease was recorded on all the plants. High disease levels on the unsprayed plants within the wall, similar to disease levels on control plants outside the wall, indicate a lack of vapour activity whereas a consistently low disease level on the unsprayed plants within the wall is good evidence of vapour activity.

Results

[X] indicates plant pot within wall having x% disease cover. Pot marked "0" in top right hand corner was sprayed with the compound of Example 13A.

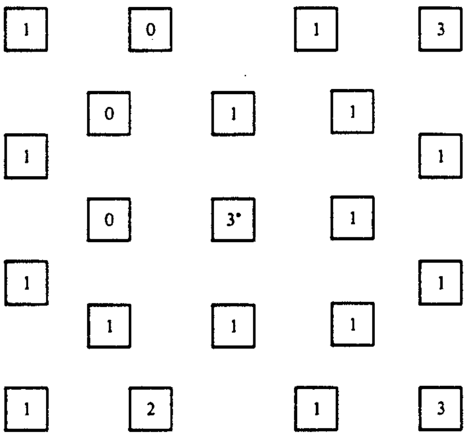

Uniformly low disease levels indicate that the compound of Example 13A exhibits vapour activity.

We claim:

1. A compound of the formula

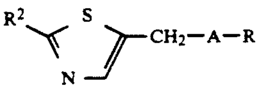

(I)

or an acid-addition salt or metal salt complex thereof, in which R represents an optionally substituted phenyl group; A represents a group $C{=}O$, $C{=}N{-}OR^1$ or 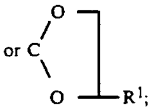

$R^1$ represents a hydrogen atom or an optionally substituted $C_{1-12}$ alkyl, $C_{1-12}$ alkenyl or benzyl group; and $R^2$ represents a hydrogen or halogen atom or a $C_{1-12}$ alkyl, $C_{1-12}$ haloalkyl, $C_{1-12}$ alkoxy, $C_{1-12}$ haloalkoxy, $C_{1-12}$ alkylthio, hydroxyl, cyano, nitro, amino, $C_{1-12}$ alkylamino or $C_{1-12}$ dialkylamino group, wherein R and $R^1$ are optionally substituted with a substituent selected from the group consisting of halogen, nitro, cyano, hydroxyl, $C_{3-8}$ cycloalkyl, $C_{1-12}$ alkyl, $C_{1-12}$ haloalkyl, $C_{1-12}$ alkoxy, $C_{1-12}$ haloalkoxy, amino, $C_{1-12}$ alkylamino, $C_{1-12}$ dialkylamino, formyl, $C_{1-12}$ alkoxycarbonyl, carboxyl, $C_{1-12}$ alkanoyl, $C_{1-12}$ alkylthio, $C_{1-12}$ alkylsulphinyl, $C_{1-12}$ alkylsulphonyl, carbamoyl, and $C_{1-12}$ alkylamido groups.

2. A compound according to claim 1 in which R represents a phenyl group substituted by 1 to 3 halogen atoms.

3. A compound according to claim 1 in which $R^1$ represents a hydrogen atom, a $C_{1-8}$ alkyl group, a $C_{2-6}$ alkenyl group or a benzyl group, each group being optionally substituted by one or more substituents selected from halogen atoms, nitro, cyano, hydroxyl, $C_{3-6}$ cycloalkyl, $C_{1-4}$haloalkyl, $C_{1-4}$alkoxy, $C_{1-4}$haloalkoxy, amino, $C_{1-4}$alkylamino, di-$C_{1-4}$alkylamino, formyl, $C_{1-4}$alkoxycarbonyl and carboxyl groups.

4. A compound according to claim 1 in which R represents a fluorophenyl or dichlorophenyl group; $R^1$ represents a hydrogen atom or a methyl, ethyl, propyl, butyl, pentyl, hexyl, heptyl, cyclopropylmethyl, allyl, benzyl, chlorobenzyl, dichlorobenzyl or bromobenzyl group; and $R^2$ represents a hydrogen atom.

5. A fungicidal composition which comprises a carrier and, as active ingredient, a compound of formula I or an acid-addition salt or metal salt complex thereof as defined in claim 1.

6. A composition according to claim 5 which comprises at least two carriers, at least one of which is a surface-active agent.

7. A method of combating fungus at a locus which comprises treating the locus with a compound of formula I, or an acid-addition salt or metal salt complex thereof, as defined in claim 1.

8. A method according to claim 7 in which the locus comprises plants subject to or subjected to fungal attack, seeds of such plants or the medium in which the plants are growing or are to be grown.

9. A method of combating fungus at a locus which comprises treating the locus with a composition as defined in claim 5.

10. A method according to claim 9 in which the locus comprises plants subject to or subjected to fungal attack, seeds of such plants or the medium in which the plant are growing or are to be grown.

* * * * *